United States Patent [19]

Cullinan et al.

[11] 4,166,810

[45] Sep. 4, 1979

[54] DERIVATIVES OF 4-DESACETYL VLB C-3 CARBOXYHYDRAZIDE

[75] Inventors: George J. Cullinan, Trafalger; Koert Gerzon, Indianapolis, both of Ind.

[73] Assignee: Eli Lilly and Company, Indianapolis, Ind.

[21] Appl. No.: 899,032

[22] Filed: Apr. 20, 1978

[51] Int. Cl.$^2$ .......................................... C07D 519/04
[52] U.S. Cl. ................................................. 260/244.4
[58] Field of Search ........................ 260/287 B, 244.4; 424/258, 262

[56] References Cited

U.S. PATENT DOCUMENTS

| | | | |
|---|---|---|---|
| 3,097,137 | 7/1963 | Beer et al. | 260/244.4 |
| 3,205,220 | 9/1965 | Suoboda et al. | 260/244.4 |
| 3,370,057 | 2/1968 | Suoboda | 260/244.4 |
| 3,387,001 | 6/1968 | Hargrove | 260/244.4 |
| 3,392,173 | 7/1968 | Hargrove | 260/244.4 |
| 3,887,565 | 6/1975 | Jones et al. | 260/244.4 |
| 3,890,325 | 6/1975 | Smith et al. | 260/244.4 |
| 3,944,554 | 3/1976 | Tafur | 260/244.4 |
| 3,954,773 | 5/1976 | Neuss et al. | 260/244.4 |
| 4,029,663 | 6/1977 | Gotowski et al. | 424/262 |
| 4,115,388 | 9/1978 | Thompson et al. | 260/244.4 |

FOREIGN PATENT DOCUMENTS 2558027  7/1976  Fed. Rep. of Germany.

*Primary Examiner*—David Wheeler
*Attorney, Agent, or Firm*—James L. Rowe; Arthur R. Whale

[57] ABSTRACT

$N^2$ derivatives of 4-desacetyl VLB (vinblastine) C-3 carboxyhydrazide, active anti-tumor agents.

6 Claims, No Drawings

DERIVATIVES OF 4-DESACETYL VLB C-3 CARBOXYHYDRAZIDE

BACKGROUND OF THE INVENTION

Several naturally-occurring alkaloids obtainable from Vinca rosea have been found active in the treatment of experimental malignancies in animals. Among these are leurosine (U.S. Pat. No. 3,370,057), vincaleukoblastine (vinblastine) to be referred to hereinafter as VLB (U.S. Pat. No. 3,097,137), leuroformine (Belgian Pat. No. 811,110); leurosidine (vinrosidine) and leurocristine (to be referred to hereafter as vincristine) (both in U.S. Pat. No. 3,205,220); deoxy VLB "A" and "B", Tetrahedron Letters, 783 (1958); 4-desacetoxyvinblastine (U.S. Pat. No. 3,954,773; 4-desacetoxy-3'-hydroxyvinblastine (U.S. Pat. No. 3,944,554); leurocolombine (U.S. Pat. No. 3,890,325) and vincadioline (U.S. Pat. No. 3,887,565). Two of these alkaloids, VLB and vincristine, are now marketed as drugs for the treatment of malignancies, particularly the leukemias and related diseases in humans. The two marketed alkaloids are customarily administered by the i.v. route.

Chemical modification of the Vinca alkaloids has been rather limited. In the first place, the molecular structures involved are extremely complex, and chemical reactions which modify one specific functional group of the molecule without affecting other groups are difficult to develop. Secondly, dimeric alkaloids lacking desirable chemotherapeutic properties have been recovered or produced from Vinca rosea fractions or alkaloids, and a determination of their structures has led to the conclusion that these "inactive" compounds are closely related to the active alkaloids, frequently differing only as to stereochemistry at a single cation. Thus, anti-neoplastic activity seems to be limited to very specific basic structures, and the chances of obtaining more active drugs by modification of these structures would seem to be correspondingly slight. Among the successful modifications of physiologically-active alkaloids has been the preparation of 6,7-dihydro VLB (U.S. Pat. No. 3,352,868) and the replacement of the acetyl group at C-4 (carbon no. 4 of the VLB ring system-see the numbered structure below) with higher alkanoyl group or with unrelated acyl groups. (See U.S. Pat. No. 3,392,173). Several of these C-4 derivatives are capable of prolonging the life of mice inoculated with P1534 leukemia. One of the C-4 derivatives in which a chloracetyl group replaces the C-4 acetyl group of VLB is also a useful intermediate for the preparation of structurally modified VLB compounds in which an N,N-dialkylglycyl group replaces the C-4 acetyl group of VLB (See U.S. Pat. No. 3,387,001). C-3 carboxamide and carboxyhydrazide derivatives of VLB, vincristine, vincadioline etc. have also been prepared and found to be active anti-tumor agents. (Belgian Pat. No. 813,168). These compounds are extremely interesting because, for example, the 3-carboxamides of VLB are more active against Ridgeway osteogenic sarcoma and Gardner lymphosarcoma than is VLB itself, the basic alkaloid from which they are derived. Certain of these amide derivatives actually approach the activity of vincristine against the same tumors. One of the amides, 4-desacetyl VLB C-3 carboxamide or vindesine, is currently on clinical trial in humans and has been found active in certain leukemias. In humans, vindesine appears to have less neurotoxicity than does vincristine and is apparently effective against vincristine-resistant leukemias.

4-Desacetyl VLB C-3 carboxyhydrazide is disclosed in Belgian Pat. No. 813,168 as being an active anti-tumor agent against transplanted tumors in mice. It has been shown to be active against Ridgeway osteogenic sarcoma, Gardner lymphosarcoma and P 1534(J) leukemia.

SUMMARY OF THE INVENTION

This invention provides compounds of the formula

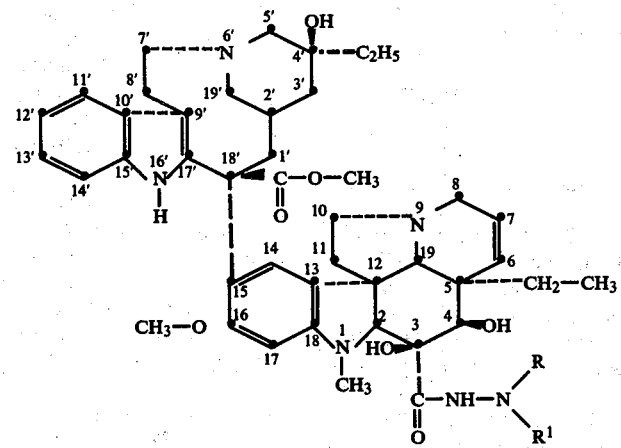

I wherein R, when taken singly, is $C_1-C_3$ alkyl, $\beta$-hydroxyethyl, $\beta$-acetoxyethyl, $C_2-C_4$ alkanoyl, dichloroacetyl, benzoyl or $C_1-C_3$ alkyl carbazyl;

$R^1$, when taken singly, is H or methyl only when R is $C_1-C_3$ alkyl and is H otherwise; and R and $R^1$, when taken together, form a $C_1-C_3$ alkylidene group.

In the above formula, R, when taken singly, can be methyl, ethyl, n-propyl, isopropyl, acetyl, propionyl, n-butyryl, isobutyryl, dichloroacetyl, benzoyl, ethyl carbazyl

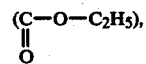

methyl carbazyl

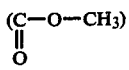

and the like groups. $C_1$–$C_3$ Alkylidene groups which R and $R^1$ represent when taken together include methylidene (=$CH_2$), ethylidene (=CH—$CH_3$), n-propylidene (=CH—$C_2H_5$) and isopropylidene

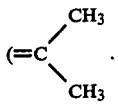

The compounds of this invention have been named as derivatives of 4-desacetyl VLB C-3 carboxhydrazide. Systematic naming of these compounds should include a "3-descarbomethoxy" term but this term has been omitted since it is implicit in the name "C-3 carboxhydrazide" in that the C-3 carbomethoxy group of VLB has been displaced. Additionally, an alternate naming system could have been employed; e.g., the compounds may be named as derivatives of 4-desacetyl VLB 23-desmethoxy-23-hydrazide referring to the replacement of the C-23 methoxyl by hydrazide. However, we prefer to name the compounds as C-3 carboxhydrazide derivatives.

Hydrazine contains two nitrogen atoms, which are numbered in a hydrazide as follows

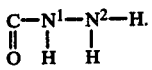

The hydrazide derivatives of this invention are all N derivatives.

The compounds of this invention having the structure of Formula I above can be prepared by several alternative procedures. The procedure that we prefer to employ involves the preparation first of 4-desacetyl VLB C-3 carboxhydrazide formed by the action of hydrazine on VLB in accordance with the procedure set forth in our copending application Ser. No. 828,693, filed Aug. 29, 1977. By this procedure, VLB and hydrazine are heated in a sealed reaction vessel employing anhydrous ethanol as a solvent. Alternatively, 4-desacetyl VLB can be reacted with anhydrous hydrazine under the same condition. The reaction of hydrazine with VLB itself serves to hydrolyze the acetoxy group at C-4 and thus the product of the reaction is invariably 4-desacetyl VLB C-3 carboxhydrazide regardless of whether VLB or 4-desacetyl VLB is employed as the starting material. The preparation of compounds of Formula I is carried out with 4-desacetyl VLB C-3 carboxhydrazide, however prepared, as a starting material. This compound is converted to the corresponding C-3 carboxazide (according to the procedure of the aforementioned patent Ser. No. 828,693) by treatment of the hydrazide with nitrite in acidic solution. 4-Desacetyl VLB C-3 carboxazide thus produced can then be reacted with various alkyl-substituted hydrazines to yield the compounds of this invention wherein R is $C_1$–$C_3$ alkyl and $R^1$ is methyl or H as provided. The azide can also be reacted with N-(β-hydroxyethyl)hydrazine to yield the corresponding 4-desacetyl VLB C-3 [$N^2$-(β-hydroxy)ethyl]carboxhydrazide. This latter compound is useful for preparing the corresponding β-acetoxy ethyl hydrazide derivative by acetylation to produce a compound according to Formula I wherein R is β-acetoxyethyl and $R^1$ is hydrogen. This latter compound is, however, preferably prepared by reacting the C-3 carboxazide with β-acetoxyethylamine.

Compounds according to Formula I wherein R is $C_2$–$C_4$ alkanoyl, dichloroacetyl, benzoyl or $C_1$–$C_3$ alkyl carbazyl are prepared by reacting 4-desacetyl VLB C-3 carbazyl with the appropriate anhydride or acid chloride. Likewise, 4-desacetyl VLB C-3 carboxhydrazide is the starting material for preparing compounds according to Formula I in which R and $R^1$ are taken together to form a $C_1$–$C_3$ alkylidene group. These compounds are prepared by reacting the unsubstituted C-3 carboxhydrazide with formaldehyde, acetaldehyde, propionaldehyde, or acetone. These alkylidene derivatives can in turn be hydrogenated as with a hydride reducing agent such as $NaBH_4$ to yield the corresponding compound according to Formula I in which R is $C_1$–$C_3$ alkyl and $R^1$ is H.

The following example more fully exemplifies the preparation of the compounds of this invention as well as required starting materials.

Preparation of Starting Materials (1) 4-Desacetyl VLB C-3 carboxhydrazide

4-Desacetyl VLB was heated in anhydrous ethanol with an excess of anhydrous hydrazine in a sealed reaction vessel at about 60° C. for about 18 hours. The reaction vessel was cooled and opened, the contents removed, and the volatile constituents evaporated therefrom in vacuo. The resulting residue, comprising 4-desacetyl VLB C-3 carboxhydrazide, was taken up in methylenechloride, the methylenechloride solution washed with water, separated and dried, and the methylenechloride removed by evaporation in vacuo. The resulting residue was dissolved in a 1:1 chloroform:benzene solvent mixture and chromatographed over silica gel. A benzene-chloroform-triethylamine eluant was employed to develop the chromatogram. The initial chromatographic fractions contained unreacted 4-desacetyl VLB. Further fractions were found to contain 4-desacetyl 18'-descarbomethoxy VLB C-3 carboxhydrazide previously described by Neuss et al., Tetrahedron Letters, 1968, 783. The next fractions, found to contain 4-desacetyl VLB C-3 carboxhydrazide by thin layer chromatography, were combined, and the solvents evaporated therefrom in vacuo. The resulting solid melted as about 219°–220° C. with decomposition.

(2) 4-Desacetyl VLB C-3 carboxazide

A solution of 678 mg. of 4-desacetyl VLB C-3 carboxhydrazide was prepared in 15 ml. of anhydrous methanol. About 50 ml. of 1 N aqueous hydrochloric acid were added, and the resulting solution cooled to about 0° C. Approximately 140 mg. of sodium nitrite were then added, and the resulting reaction mixture stirred for 10 minutes while maintaining the temperature at about 0° C. The solution turned dark red-brown upon the addition of the sodium nitrite. The reaction mixture was next made basic by the addition of an excess of cold 5 percent aqueous sodium bicarbonate. The aqueous solution was extracted three times with methylene dichloride. 4-Desacetyl VLB C-3 carboxazide formed in the above reaction passed into the methylene dichloride. The methylene dichloride solution of 4-desacetyl vinblastine C-3 carboxazide ordinarily is used without further purification.

EXAMPLE 1

Preparation of 4-Desacetyl VLB C-3 $N^2$-methylcarboxhydrazide 20 ml. of $CH_3NHNH_2$ were added to a solution containing approximately one gram of 4-desacetyl VLB C-3 carboxazide in 150 ml. of $CH_2Cl_2$. The reaction vessel was sealed and allowed to remain at room temperature for 6 hours. The $CH_2Cl_2$ solution was then extracted several times with water to remove excess $CH_3NHNH_2$. The $CH_2Cl_2$ solution was dried and the solvent evaporated in vacuo. The resulting tan amorphous solid comprising 4-desacetyl VLB C-3 $N^2$-methylcarboxhydrazide had the following physical data:

M.S.: m/e = 782 (M+), 441, 355, 154
I.R.: $\nu$ 3450 cm$^{-1}$ (—N—H) 1715 cm$^{-1}$ (—COOCH$_3$) 1655 cm$^{-1}$ (—COONH—)

EXAMPLE 2

Preparation of 4-Desacetyl VLB C-3 $N^2$-ethylidenecarboxhydrazide

One millimole (768 mg) of 4-desacetyl C-3 carboxhydrazide was dissolved in 50 ml. of $CH_2Cl_2$ and 200 mg. of $CH_3CHO$ were added. The reaction vessel was sealed and allowed to remain overnight at room temperature. The solution was evaporated down to a tan amorphous powder which was partitioned between $CH_2Cl_2$ and water to remove excess $CH_3CHO$. The $CH_2Cl_2$ solution was dried and evaporated to dryness. The resulting tan, amorphous powder comprising 4-desacetyl VLB C-3 $N^2$=ethylidenecarboxhydrazide had the following physical data:

M.S.: m/e = 794 (M+)
I.R.: $\nu$(CON) 1680 cm$^{-1}$ (COO) 1710 cm$^{-1}$

EXAMPLE 3

Preparation of 4-Desacetyl VLB C-3 $N^2$-ethylcarboxhydrazide

4-Desacetyl VLB C-3 $N^2$-ethylidenecarboxhydrazide from Example 2 was dissolved in 100 ml. of absolute EtOH and 500 mg. of 96% $NaBH_4$ were added. The reaction was stirred overnight at room temperature. 1 N HCl was added to the reaction until the solution cleared. Additional water was then added. The solution was made basic with conc. $NH_4OH$ and extracted twice with $CH_2Cl_2$. The $CH_2Cl_2$ extracts were dried and evaporated to dryness. The resulting, tan, amorphous powder comprising 4-desacetyl VLB C-3 $N^2$-ethylcarboxhydrazide had the following physical characteristics:

M.S.: m/e = 796 (M+)
I.R.: $\nu$(N—H) 3460 cm$^{-1}$ (CON) 1656 cm$^{-1}$ (COO) 1715 cm$^{-1}$

EXAMPLE 4

Preparation of 4-Desacetyl VLB C-3 $N^2,N^2$-dimethylcarboxhydrazide

To a solution of approximately 1.5 g. of 4-desacetyl VLB C-3 carboxazide in $CH_2Cl_2$ were added 20 ml. of $H_2NN(CH_3)_2$. The reaction vessel was sealed and allowed to remain for about 60 hours at room temperature. The resulting solution was evaporated to dryness and dissolved in $CH_2Cl_2$. The $CH_2Cl_2$ solution was extracted once with dilute $NH_4OH$ and again with water to remove excess $H_2NN(CH_3)_2$. The $CH_2Cl_2$ solution was dried and evaporated to dryness. The resulting powder was chromatographed over silica gel and eluted with EtOAc-MeOH(1:1). The fractions containing the desired product as determined by thin-layer chromatography (silica-gel eluted with EtOAc-MeOH[1:1]) were combined and the combined fractions evaporated to dryness. The resulting, tan, amorphous powder comprising 4-desacetyl VLB C-3 $N^2,N^2$-dimethylcarboxhydrazide had the following physical characteristics:

M.S.: m/e 796 (M+), 737, 455, 355, 154
I.R.: $\nu$(COO) 1715 cm$^{-1}$ (CON) 1670 cm$^{-1}$

EXAMPLE 5

Preparation of 4-Desacetyl VLB C-3 $N^2$-acetylcarboxhydrazide 300 mg. of acetic anhydride were added to a solution of 1500 mg. of 4-desacetyl VLB C-3 carboxhydrazide which had been dissolved in 50 ml. of $CH_2Cl_2$. The reaction mixture was kept for 3 hours at room temperature. The $CH_2Cl_2$ solution was then washed with dil. $NH_4OH$ and again with water. The $CH_2Cl_2$ solution was dried and evaporated to dryness. The resulting tan, amorphous powder comprising 4-desacetyl VLB C-3 $N^2$-acetyl carboxhydrazide had the following physical characteristics:

M.S.: m/e = 810 (M+)
I.R.: $\nu$(N—H) 3410 cm$^{-1}$ (COO) 1720 cm$^{-1}$ (CON) 1670 cm$^{-1}$

4-Desacetyl VLB C-3 $N^2$-dichloroacetylcarboxhydrazide is prepared in similar fashion by substituting dichloroacetic anhydride for acetic anhydride.

EXAMPLE 6

Preparation of 4-Desacetoxy VLB C-3 $N^2$-butyrylcarboxhydrazide 120 mg. of butyric anhydride were added to a solution of 768 mg. of 4-desacetyl VLB C-3 carboxhydrazide dissolved in 50 ml. of $CH_2Cl_2$. The reaction vessel was sealed and allowed to remain overnight at room temperature. The reaction was then extracted with dilute $NH_4OH$ and the extract discarded. The remaining $CH_2Cl_2$ solution was dried and evaporated to dryness. The residue was chromatographed over silica gel eluted with EtOAc-MeOH(1:1). Fractions containing the desired product as determined by TLC were combined and the combined fractions evaporated to dryness. The resulting tan, amorphous powder (128 mg.) comprising 4-desacetyl VLB C-3 $N^2$-butyrylcarboxhydrazide had the following physical characteristics:

M.S.: m/e = 838 (M+), 497, 355, 154

EXAMPLE 7

Preparation of 4-Desacetyl VLB C-3 $N^2$-benzoylcarboxhydrazide

To a solution of 768 mg. of 4-desacetyl VLB C-3 carboxhydrazide dissolved in 50 ml. of $CH_2Cl_2$, were added 240 mg. of benzoic anhydride. The reaction vessel was sealed and allowed to remain overnight at room temperature. The reaction vessel was opened and the $CH_2Cl_2$ solution therein was washed with dilute $NH_4OH$ and subsequently with water to remove benzoate salts. The $CH_2Cl_2$ solution was then dried and evaporated to dryness. The amorphous powder was chromatographed over silica gel eluted with EtOAc-MeOH(1:1). Fractions containing the desired product was determined by TLC (silica with EtOAc-MeOH[1:1]) were combined and evaporated to dryness.

The resulting, tan amorphous powder comprising 4-desacetyl VLB C-3 $N^2$-benzoylcarboxhydrazide had the following physical characteristics:

M.S.: m/e=872 (M+), 813, 531, 355, 154
NMR: consistent with proposed structure; new aromatic protons at δ7.3–8.0.

EXAMPLE 8

Preparation of 4-Desacetyl VLB C-3 $N^2$-(β-hydroxy)ethylcarboxhydrazide

Approximately 3 g. of 4-desacetyl VLB C-3 carboxazide were dissolved in $CH_2Cl_2$ and 15 ml. of $H_2NNHCH_2CH_2OH$ were added. The reaction vessel was sealed and stirred overnight at room temperature. The reaction mixture was evaporated and the residue partitioned between $CHCl_3$ and $H_2O$. The $CHCl_3$ solution was washed twice with water, dried and evaporated to dryness. The amorphous powder was chromatographed over silica gel eluted with EtOAc-MeOH(1:1). Fractions containing the desired product as determined by TLC (silica gel eluted with EtOAc-MeOH[1:1]) were combined and the combined fractions evaporated to dryness. The resulting tan, amorphous powder had the following physical characteristics:

I.R.: $\nu$(COO) 1720 cm$^{-1}$ (CON) 1655 cm$^{-1}$
NMR: NMR consistent with proposed structure

EXAMPLE 9

Preparation of 4-desacetyl VLB C-3 $N^2$-(β-acetoxy)ethylcarboxhydrazide 1624 mg. of 4-Desacetyl VLB C-3 $N^2$-(βhydroxy)ethylcarboxhydrazide were dissolved in 50 ml. of $CH_2Cl_2$. To this solution were added 220 mg. of acetic anhydride. The reaction vessel was sealed and allowed to remain overnight at room temperature. The reaction mixture was then washed with dilute $NH_4OH$ and with water. The resulting $CH_2Cl_2$ solution was dried and evaporated to dryness. The amorphous powder was chromatographed over silica gel, and the chromatogram eluted with EtOAc-MeOH[1:1]. Fractions containing the desired product as determined by TLC (silica gel eluted with EtOAc-MeOH[1:1]) were combined and the combined fractions evaporated to dryness. The resulting tan, amorphous powder (215 mg.) comprising 4-desacetyl VLB C-3 $N^2$-(β-acetoxy)ethylcarboxhydrazide had the following physical characteristics:

M.S.: m/e=854(M+), 795, 651, 513, 355, 154

EXAMPLE 10

Preparation of 4-Desacetyl VLB C-3 $N^2$-ethylcarbazylcarboxhydrazide

Approximately 900 mg. of 4-desacetyl VLB C-3 carboxazide were dissolved in $CH_2Cl_2$. 1 g. of

was dissolved in $CH_2Cl_2$ and added to the above solution. The reaction vessel was sealed and allowed to remain overnight at room temperature. The reaction mixture was then evaporated to dryness and the residue partitioned between $CH_2Cl_2$ and water. The $CH_2Cl_2$ layer was washed twice more with water, dried and evaporated to dryness. The resulting tan, amorphous powder comprising 4-desacetyl VLB C-3 $N^2$-ethylcarbazylcarboxhydrazide was converted to its sulfuric acid salt by dissolving the amorphous powder in anhydrous ethanol and then adjusting the pH to approximately 4 with 2% $H_2SO_4$ in absolute alcohol. The sulfate precipitated, was collected by filtration and dried. The resulting material was a tan, amorphous powder (104 mg.).

EXAMPLE 11

Preparation of 4-Desacetyl VLB C-3 $N^2$-methylidenecarboxhydrazide 768 mg. of 4-Desacetyl VLB C-3 carboxhydrazide were dissolved in 100 ml. of THF and 20 ml. of 37% HCHO in water were added. The reaction vessel was sealed and was stirred overnight at room temperature. The reaction solution was evaporated to a gel which was subsequently dissolved in absolute EtOH. To the alcohol solution, $CH_2Cl_2$ was added and the resulting solution was extracted with water. The $CH_2Cl_2$ solution was separated, dried and evaporated to dryness. The resulting tan, amorphous powder comprising 4-desacetyl VLB C-3 $N^2$-methylidenecarboxhydrazide had the following physical characteristics:

M.S.: m/e=780 (M+), 439, 355, 154
I.R.: broad band for carbonyls $\nu$1650–1740 cm$^{-1}$
NMR: two new signals δ4.63 and δ4.89

The compounds of this invention are active in inhibiting the growth of transplanted tumors in mice and/or in prolonging the life of tumor-innoculated mice. In demonstrating activity of these drugs, a protocol was used which involved administration of the drug, usually by the intraperitoneal route at a given dose level for 7–10 days. The size of the tumor was measured at 7 or 11 days where the drug inhibited tumor growth. Where life-prolongation was concerned, extra life span of treated animals over that of control animals was determined.

The following table—Table 1—gives the results of experiments in which mice bearing transplanted tumors were treated successfully with a compound of this invention. In the table, column 1 gives the name of the compound; column 2, the transplanted tumor; column 3, the dose level or dose level range and the number of days the dosage was administered; and column 4, the percent inhibition of tumor growth or percent prolongation of survival time, e.g., B16 (ROS is an abbreviation for Ridgeway osteogenic sarcoma; GLS for Gardner lymphosarcoma; P 1534 (J) for a leukemia and B16 (J) for a malignant melanoma.

TABLE 1

| Compound | Tumor | Dose mg/kg. × days | Percent Inhibition or Prolongation | |
|---|---|---|---|---|
| | | | 7 days | 11 days |
| 4-Desacetyl VLB C-3 $N^2$-methylcarboxhydrazide | GLS | 0.25–0.5 × 10 | Toxic | Toxic |
| | | 0.125 × 10 | 83 | 53 |
| 4-Desacetyl VLB C-3 $N^2$, $N^2$-dimethylcarboxhydrazide | GLS | 0.5 × 10 | Toxic | Toxic |

TABLE 1-continued

| Compound | Tumor | Dose mg/kg. × days | Percent Inhibition or Prolongation | |
|---|---|---|---|---|
| | | | 7 days | 11 days |
| | | 0.25 × 10 | 100 | — |
| | | 0.125 × 10 | 100 | 93 |
| 4-Desacetyl VLB C-3 N²-ethylcarboxhydrazide | GLS | 0.5 × 10 | Toxic | Toxic |
| | | 0.25 × 10 | 100 (+) | Toxic |
| 4-Desacetyl VLB C-3 N²-(β-hydroxy)ethylcarboxhydrazide | GLS | 0.5 × 10 | Toxic | Toxic |
| | | 0.5 × 7 | 90 | |
| | | 0.3 × 7 | 20 | |
| | | 0.25 × 10 | 100 | 40 |
| | | 0.125 × 10 | 77 | 37 |
| | | 0.2 × 7 | | |
| | | 0.3 × 9 | 17 | |
| | | 0.2 × 9 | 100 | |
| | | 0.1 × 9 | 0 | |
| | ROS | 0.5 × 10 | Toxic | |
| | | 0.3 × 10 | 14 | |
| | | 0.2 × 10 | 0 | |
| 4-Desacetyl VLB C-3 N²-(β-acetoxy)ethylcarboxhydrazide | GLS | 0.5 × 10 | 100 | 100 |
| | | 0.25 × 10 | 100 | 73 |
| | | 0.125 × 10 | 74 | 26 |
| VLB C-3 N²-(β-acetoxy)ethylcarboxhydrazide | GLS | 0.5 × 10 | 100 | 87 |
| | | 0.25 × 10 | 74 | 55 |
| | | 0.125 × 10 | 36 | 35 |
| 4-Desacetyl VLB C-3 N²-acetylcarboxhydrazide | GLS | 0.5 × 10 | 100 | Toxic |
| | | 0.25 × 10 | 100 | 100 |
| | | 0.125 × 10 | 100 | 93 |
| | B16 | 1.2 × 3 | | 69 |
| | | 0.9 × 3 | | 84 |
| | | 0.6 × 3 | | 109 |
| | | 0.3 × 3 | | 100 |
| | | 0.15 × 3 | | 71 |
| 4-Desacetyl VLB C-3 N²-benzoylcarboxhydrazide | GLS | 0.5 × 10 | Toxic | Toxic |
| | | 0.25 × 10 | 100 | Toxic |
| | | 0.125 × 10 | 76 | 45 |
| 4-Desacetyl VLB C-3 N²-butyrylcarboxhydrazide | GLS | 0.5 × 10 | 64 | Toxic |
| | | 0.25 × 10 | 100 | 100 |
| | | 0.125 × 10 | 100 | 100 |
| 4-Desacetyl VLB C-3 N²-ethylcarbazylcarboxhydrazide | GLS | 0.4 × 7 | 93 | |
| | | 0.2 × 7 | 100 | |
| | ROS | 0.4 × 10 | Toxic | |
| | | 0.2 × 10 | 66 | |
| 4-Desacetyl VLB C-3 N²-isopropylidenecarboxhydrazide | ROS | 0.05 × 10 | 33 | |
| | | 0.1 × 10 | 42 | |
| | | 0.15 × 10 | 74 | |
| | | 0.2–1.0 × 10 | Toxic | |
| 4-Desacetyl VLB C-3 N²-ethylidenecarboxhydrazide | GLS | 0.4 × 9 | Toxic | |
| | | 0.2 × 9 | 100 | |
| | ROS | 0.4 × 9 | Toxic | |
| | | 0.2 × 9 | 100 | |
| 4-Desacetyl VLB C-3 N²-methylidenecarboxhydrazide | GLS | 0.5 × 10 | Toxic | Toxic |
| | | 0.25 × 10 | 100 | 100 |
| | | 0.125 × 10 | 91 | 91 |

As would be expected, the novel hydrazide derivatives of this invention differ in their anti-tumor spectrum from VLB, vincristine and vindesine, as well as from the C-4 N,N-dialkylglycyl esters of VLB, in the same way that the anti-tumor spectra of those compounds differ among themselves, some being more effective against certain tumors or classes of tumors and less effective against others. However, in utilizing a compound of this invention clinically, the clinical physician would administer it initially by the same route and in the same vehicle and against the same types of tumors as for clinical use of vincristine and VLB. Differences in dosage level would, of course, be based on relative activity between vincristine or VLB and the new drug in the same experimental tumor in mice.

In utilizing the novel hydrazide derivatives of this invention as anti-neoplastic agents, the parenteral route of administration would be employed. For this purpose, isotonic solutions are employed containing 1–10 mg./ml. of a compound of this invention. The compounds are administered at the rate of from 0.01 to 1 mg./kg. and preferably from 0.1 to 1 mg./kg. of mammalian body weight once or twice a week or every two weeks depending on both the activity and the toxicity of the drug. An alternative method of arriving at a therapeutic dose is based on body-surface area with a dose in the range 0.1 to 10 mg./meter squared of mammalian body surface every 7 or 14 days.

A clinical trial of a compound of this invention would be carried out in accordance with a procedure suggested by S. K. Carter in a section headed "Study Design Principles for the Clinical Evaluation of New Drugs as Developed by the Chemotherapy Programme of the National Cancer Institute" to be found on pages 242–289 of a recent book "The Design of Clinical Trials in Cancer Therapy" edited by Maurice Staguet (Futura Publishing Co., New York, 1973).

We claim:

1. A compound of the formula

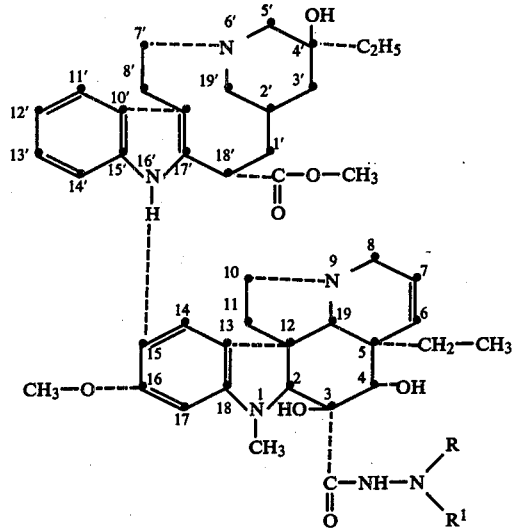

wherein R, when taken singly, is β-hydroxyethyl, β-acetoxyethyl, $C_2$–$C_4$ alkanoyl, dichloroacetyl, benzoyl or $C_1$–$C_3$ alkyl carbazyl;

$R^1$, when taken singly, is H; and

R and $R^1$, when taken together, form a $C_1$–$C_3$ alkylidene group.

2. A compound according to claim 1, said compound being 4-desacetyl VLB C-3 $N^2$-methylidenecarboxhydrazide.

3. A compound according to claim 1, said compound being 4-desacetyl VLB C-3 $N^2$-isopropylidenecarboxhydrazide.

4. A compound according to claim 1, said compound being 4-desacetyl VLB C-3 $N^2$-butyrylcarboxhydrazide.

5. A compound according to claim 1, said compound being 4-desacetyl VLB C-3 $N^2$-acetylcarboxhydrazide.

6. A compound according to claim 1, said compound being 4-desacetyl VLB C-3 $N^2$-(β-hydroxy)ethylcarboxhydrazide.

* * * * *